United States Patent [19]

Pagnotta et al.

[11] Patent Number: 4,568,782

[45] Date of Patent: Feb. 4, 1986

[54] PREPARATION OF INDENES

[75] Inventors: Marco Pagnotta, University Heights; Mark C. Cesa, South Euclid; James D. Burrington, Richmond Heights, all of Ohio

[73] Assignee: The Standard Oil Company, Cleveland, Ohio

[21] Appl. No.: 745,963

[22] Filed: Jun. 17, 1985

[51] Int. Cl.$^4$ ............................ C07C 1/20; C07C 1/00
[52] U.S. Cl. ...................................... 585/409; 585/358; 260/455 R; 560/139; 560/238; 564/428; 568/38; 568/317; 568/327; 568/632; 570/199; 570/201
[58] Field of Search .................... 260/455 R; 560/139, 560/238; 564/428; 568/38, 58, 317, 327, 529, 632; 570/199, 201; 585/409, 408, 407, 358, 357

[56] References Cited

U.S. PATENT DOCUMENTS 3,210,433 10/1965 Chibnik ............................... 585/409
4,232,178 11/1980 Schaper et al. ...................... 585/409

FOREIGN PATENT DOCUMENTS 625240 8/1961 Canada ................................ 585/408
513962 7/1974 U.S.S.R. ............................. 585/409

*Primary Examiner*—John Doll
*Assistant Examiner*—A. Pal
*Attorney, Agent, or Firm*—Charles S. Lynch; John E. Miller; Larry W. Evans

[57] ABSTRACT

Disclosed is the vapor phase cyclodehydration of an aldehyde or ketone over a solid Lewis acid as catalyst to make indene or a substituted indene according to the equation:

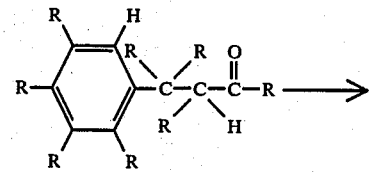

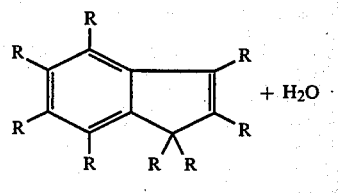

$+ H_2O$

9 Claims, No Drawings

PREPARATION OF INDENES

The present invention relates to the preparation of indene or substituted indenes by the vapor phase catalytic cyclodehydration of 3-phenylpropionaldehydes and 3-phenylpropylketones.

Indenes are currently prepared industrially by isolation from coal tar or petroleum distillates. This method yields indene of too low a purity to be useful for preparation of high HDT polymers without extensive and costly purification. High purity indene is not currently an item of commerce in more than research quantities. Syntheses of indene have traditionally relied upon cumbersome, multi-step, non-catalytic methods which are not industrially useful because of their inherently low yields and poor product recovery as well as their requirement of highly acidic reaction conditions (see, for example, Wittig. G. Chem. Ber. 91, 1958. 895 or Waldman and Schwenk, Ann. 487, 1931, 287; or Ulman and Lehner, Ber. 38, 1905, 729; or Weedon and *Wahler, J.Am.Chem.Soc.* 33, 1905, 386.

It is an object of the present invention to provide a process for making indenes synthetically.

It is a further object to provide a one step process for making indenes from relatively inexpensive starting materials in a single reaction step.

Other objects, as well as aspect, features, and advantages, of the invention will be apparent from the disclosure and claims.

These and other objects are realized by the present invention according to which there is provided a process for the synthesis of indene and substituted indenes by the catalytic cyclodehydration of substituted and unsubstituted 3-phenylpropionaldehydes and 3-phenylpropylketones, according to the equation:

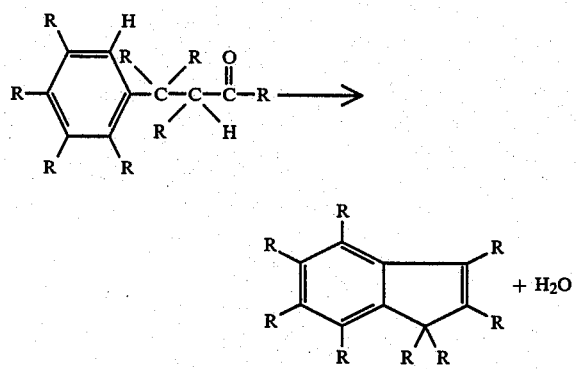

wherein no R group contains ethylenic or acetylenic unsaturation, wherein the R group attached to the carbonyl group is selected from H and hydrocarbyl and each of the remaining R groups is selected independently from hydrogen, halo, nitro, trihalomethyl, acyl, acyloxy, acylthio, lower alkyl secondary amino where each alkyl has 1–4 C atoms, and hydrocarbyl, hydrocarbyloxy and hydrocarbylthio having 1–10 C atoms; wherein hydrocarbyl ring(s) can be formed from one or more adjacent pairs of R groups on the benzene ring; and wherein one of the R groups attached to the benzylic carbon can form a hydrocarbyl ring with the R group attached to the ortho position, said cyclodehydration being effected by passing the starting material aldehyde or ketone in the vapor phase over a solid catalyst which is a Lewis acid.

In the foregoing process the substrate aldehyde or ketone usually has 9–35 C atoms. Of these, a useful group of substrates are those wherein the R groups not on the benzene ring are independently chosen from H and methyl, and in particularly those in which the R groups in the benzene ring are also independently chosen from H and methyl, especially those where such R groups all are H.

Our vapor phase cyclodehydration reaction is effected usually in the temperature range 50°–600° C., more usually in the range 200°–500° C.

Very useful catalysts are solid Lewis acids such as $BPO_4$, $AlPO_4$, and particularly the acidic zeolites, for instance, mordenite and ZSM-5 type zeolites. Other examples of acidic solids useful as catalysts are $AlCl_3$, $B_2O_3.Al_2O_3$, bentonite, $Ti_3(PO_4)_4$, and $FePO_4$.

Although acid catalyzed cyclizations of 3-phenyl substituted acids or acid derivatives to indanones are well known, subsequent indene formation requires an additional and potentially costly reductive dehydration. An especially attractive alternative, briefly studied nearly a century ago, is the direct formation of indene or a substituted indene by cyclization and subsequent in situ dehydration of 3-phenyl substituted aldehydes or ketones. For example, Miller and Rohde as early as 1892, Ber. 1892, 23, 1881–1886, reported a 3.8 percent isolated yield of γ-methylindene from the reaction of 4-phenyl-2-butanone (benzylacetone) with a 30-fold molar excess of concentrated sulfuric acid. Under identical conditions, 4-phenyl-3-methyl-2-butanone gave dimethylindene in unspecified yields.

Similarly, 5-amino-2-methylindene was prepared from the reductive cyclization of 3-(m-nitrophenyl)-2-methylpropionaldehyde with zinc and hydrochloric acid at elevated temperatures. Miller W. v. and Kinkelin G. Ber. 1886, 19, 1249 and 1520; Miller, W. v. and Rohde, G. ibid 1889, 22, 1830–1843. The difunctional 3-carboxy-4-phenyl-2-butanone reacted with excess sulfuric acid to give an unspecified yield of 1-methyl-2-carboxyindene. Roser, W. Ber. 1887, 20, 1574–1576.

These homogenous reactions, using a stoichiometric excesses of liquid acids, seem to be the only prior art on this subject.

We regard the catalytic conversion of the defined aldehydes and ketone substrates to indenes in the vapor phase over a solid acid heterogeneous catalyst as defining our broad invention. The discovery of such reactions using solid acid catalysts has obvious advantages over the prior art reactions using very large volumes of strong and corrosive liquid inorganic acids. Moreover, the prior art authors indicate that such cyclization can only occur when the substrate has a sidechain on the carbon γ to the carbonyl group, and for aldehydes, additionally only when a m-nitro substituent is present. In fact, Roser, cited above, explicitly states that indene itself cannot be prepared directly from 3-phenylpropionaldehyde.

The aldehyde and ketone starting materials of the invention can be prepared by well-known methods. For example, linear hydroformylation of styrene and its derivatives yields the corresponding 3-phenylpropionaldehyde (see, for example U.S. Pat. No. 4,052,461 or U.S. Pat No. 4,268,688 or Lai, R. and Ucciaini, E., *J. Molec. Catal.*, 1978, 4, 401–10; and Cornvil, V. B. and Payer, R., *Chem. Zeitung*, 1974, 98, 596–606.)

In carrying out the process, the aldehyde or ketone is vaporized and passed over the aforementioned solid catalyst, suitably in a fixed bed configuration at temperatures in the range of 50°–600° C., usually 200°–500° C.

A non-reactive carrier vapor or diluent gas can be used but is not required. When such a diluent is used the concentration of the substrate in the total feed is usually in the range of from 0.1 to 50 volume percent, although higher or lower concentrations can be employed, of course including undiluted substrate vapor. The desired product as well as any unreacted starting materials can be isolated directly from the effluent stream.

Examples of diluents useful in the present process include helium, argon, nitrogen and water (steam).

Contact times used are 0.01–100 sec. usually 0.1–10 sec. (average time for 1 volume of feed to pass over an equal volume of catalyst).

The products of the invention, indene or the defined substituted indenes, have varied uses. All of the products of the present invention are polymerizable to solid thermoplastic polymers useful to mold utilitarian objects, such as tumblers, plates, containers, etc.

The polymerization can be effected using $BF_3$, $TiCl_4$, $SnCl_4$ or $SnCl_5$ as catalysts at low temperatures by the method of Plyusnin, Babin and Chertkova in Zh. Prikl. Khim. 29. 1070 (1956.)

The following specific examples of the invention are merely illustrative and are not to be considered limiting. In effecting the runs of the examples, a stainless steel, fixed-bed upward flow reactor was charged with the particulate catalyst and placed into a molten salt bath set at the desired reaction temperature; a carrier gas of argon or nitrogen was fed through the reactor at the desired rate and the aldehyde or ketone was continuously added at the desired rate. Products were isolated by passing the effluent stream through ice-cold tetrahydrofuran. The resulting solution was directly analyzed by gas chromatograph. The volume ratio of aldehyde to diluent gas was 1:25.

Examples 1–13 are shown in Table 1 in tabular form.

EXAMPLE 15

Example 14 was repeated except that 4-phenyl-2-pentanone was the starting material, 1,3-dimethylindene was present in the reactor effluent.

EXAMPLE 16

Example 14 was repeated except that 4-phenyl-4-methyl-2-pentanone was the starting substrate. In the product was a yield of less than 10 percent of a product having a molecular weight of 158 consisting of four isomers, one of which was 1,1,3-trimethylindene.

EXAMPLE 17

Using the procedure before outlined 3-phenylbutanal was reacted over the same catalyst as Example 9 at 400° C. at a contact time of 0.80 second. The diluent was argon. A 32 percent yield of 1-methylindene and a 10 percent yield of 3-methylindene was obtained. Conversion was 99 percent.

As will be evident to those skilled in the art various modifications of this invention can be made or followed in the light of the foregoing disclosure and discussion without departing from the spirit and scope of the disclosure or from the scope of the claims.

We claim:

1. A process for the synthesis of indene and substituted indenes by the catalytic cyclodehydration of a substrate substituted and unsubstituted 3-phenylpropionaldehydes and 3-phenylpropylketones, according to the equation:

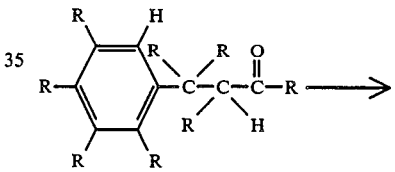

TABLE I

| | Cyclodehydration of 3-phenylpropionaldehyde | | | | | | |
|---|---|---|---|---|---|---|---|
| Example No. | Catalyst | Temp. °C. | Contact Time Secs. | Diluent | Conversion % | Selectivity to Indene % | Yields % Indene | Indane |
| 1 | AlPO$_4$ | 300 | 1.55 | N$_2$ | 96.0 | 6.6 | 6.3 | 0.6 |
| 2 | BPO$_4$ | 300 | 0.73 | N$_2$ | 39.3 | 53.5 | 21.0 | 0.1 |
| 3 | Z2OOH$^e$ | 275 | 1.84 | Ar | 38.3 | 43.6 | 16.7 | 0.4 |
| 4 | Z2OOH$^e$ | 300 | 1.75 | Ar | 38.3 | 69.7 | 26.7 | 0.6 |
| 5 | Z2OOH$^f$ | 300 | 1.75 | Ar | 56.0 | 42 | 23.5 | 0.5 |
| 6 | Z2OOH$^e$ | 325 | 1.68 | Ar | 46.3 | 67.4 | 31.2 | 0.3 |
| 7 | Z2OOH$^e$ | 350 | 1.61 | Ar | 61.9 | 72.7 | 45.0 | 1.0 |
| 8 | Z2OOH$^e$ | 375 | 1.55 | Ar | 73.6 | 76.1 | 56.0 | 1.7 |
| 9 | Z2OOH$^e$ | 400 | 1.49 | Ar | 92.7 | 78.6 | 72.9 | 3.0 |
| 10 | Z2OOH$^e$ | 425 | 1.44 | Ar | 97.9 | 79 | 77.3 | 3.5 |
| 11 | Z2OOH$^e$ | 375 | 1.55 | Ar | 31.0 | 43.5 | 13.5 | 1.5 |
| 12 | Z82$^g$ | 400 | 1.49 | Ar | 97.9 | 6.6 | 6.5 | 7.2 |
| 13 | Z—Y$^h$ | 400 | 1.49 | Ar | 94.0 | 29 | 27.3 | 11.9 |

$^e$1/16" extrudates of mordenite type zeolite;
$^f$pulverized mordenite type zeolite;
$^g$1/16" extrudates of Y type zeolite;
$^h$1/16" extrudates of Y type zeolite impregnated with rare earth oxides.

EXAMPLE 14

Using the procedure before outlined 4-phenyl-2-butanone (benzylacetone) was reacted over the same catalyst as Example 9 at 400° C. at a contact time of 1.49 seconds. The diluent was argon. A 50.0 percent yield of 1- and 3-methylindenes resulted, about equal molar amounts of each. Conversion was nearly 100 percent.

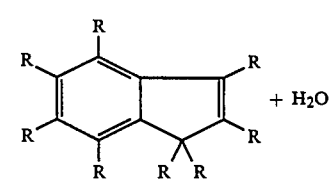

wherein no R group contains ethylenic or acetylenic unsaturation; wherein the R group attached to the carbonyl group is selected from H and hydrocarbyl and each of the remaining R groups is selected independently from hydrogen. halo, nitro. trihalomethyl, acyl, acyloxy, acylthio, lower alkyl secondary amino where each alkyl has 1-4 C atoms. and hydrocarbyl. hydrocarbyloxy and hydrocarbylthio having 1-10 C atoms; wherein hydrocarbyl ring(s) can be formed from one or more adjacent pairs of R groups on the benzene ring; and wherein one of the R groups attached to the benzylic carbon can form a hydrocarbyl ring with the R group attached to the ortho position, said cyclodehydration being effected by passing the starting material aldehyde or ketone in the vapor phase over a solid Lewis acid as catalyst.

2. A process accordng to claim 1 wherein said substrate contains 9-35 C atoms.

3. A process according to claim 1 wherein the temperature of the cyclodehydration reaction is in the range from 50-600° C.

4. A process according to claim 1 wherein the temperature of the cyclodehydration reaction is in the range from 200-500° C.

5. A process of claim 4 wherein the contact time is in the range from 0.01-100 seconds.

6. A process of claim 4 wherein the contact time is 0.1-10 seconds.

7. A process according to claim 2 wherein the R groups not on the benzene ring are independently chosen from H and methyl.

8. A process according to claim 7 wherein all R groups on the benzene ring are H.

9. A process according to claim 1 wherein said substrate is 3-phenylpropionaldehyde and the product of said synthesis is indene.

* * * * *